United States Patent [19]

Brodack et al.

[11] Patent Number: 5,560,901
[45] Date of Patent: * Oct. 1, 1996

[54] RADIONUCLIDE LABELLED PARTICLES USEFUL FOR RADIATION SYNOVECTOMY

[75] Inventors: James W. Brodack, Florissant; Edward A. Deutsch; Karen F. Deutsch, both of Maryland Heights; Dennis L. Nosco, Florissant, all of Mo.

[73] Assignee: Mallinckrodt Medical, Inc., St. Louis, Mo.

[*] Notice: The portion of the term of this patent subsequent to Jun. 14, 2011, has been disclaimed.

[21] Appl. No.: 215,332

[22] Filed: Mar. 21, 1994

Related U.S. Application Data

[63] Continuation-in-part of Ser. No. 47,322, Apr. 16, 1993, Pat. No. 5,320,824, which is a continuation-in-part of Ser. No. 631,580, Dec. 21, 1990, abandoned, which is a continuation-in-part of Ser. No. 420,795, Oct. 12, 1989, abandoned.

[51] Int. Cl.$^6$ .......................... A61K 51/00; A61K 51/12
[52] U.S. Cl. .................. 424/1.29; 424/1.33; 424/1.37
[58] Field of Search ..................... 424/1.29, 1.33, 424/1.37

[56] References Cited

U.S. PATENT DOCUMENTS

| | | | |
|---|---|---|---|
| 5,137,709 | 8/1992 | Simon et al. | 252/625 X |
| 5,300,281 | 4/1994 | McMillan et al. | 424/1.29 |
| 5,320,824 | 6/1994 | Brodack et al. | 424/1.29 X |

Primary Examiner—John Kight
Assistant Examiner—Lara E. Chapman
Attorney, Agent, or Firm—Thomas P. McBride; Roy J. Klostermann; Brian K. Stierwalt

[57] ABSTRACT

The present invention provides radiation synovectomy compositions for treating inflamed synovium containing a radionuclide complex bound to a hydroxyapatite-like matrix as the radiolabelled synovectomy agent in a sufficient amount to provide satisfactory synovectomy of the inflamed synovium together with a pharmaceutically acceptable vehicle, the radionuclide being a beta emitter that will substantially ablate the inflamed synovium, but not significantly damage underlying articular cartilage, the radionuclide complex being substantially kinetically stable, and if said radionuclide or radionuclide complex leaks from said joint it will be excreted from the body, the agent having a particle size such that there is essentially little or no leakage of the radionuclide complex from the joint after administration.

12 Claims, No Drawings

5,560,901

RADIONUCLIDE LABELLED PARTICLES USEFUL FOR RADIATION SYNOVECTOMY

CROSS REFERENCE TO RELATED APPLICATION

This application is a continuation-in-part of application Ser. No. 08/047,322, filed Apr. 16, 1993, now U.S. Pat. No. 5,320,824, which is a continuation-in-part of application Ser. No. 07/631,580, filed Dec. 21, 1990, now abandoned, which is a continuation-in-part of application Ser. No. 08/420,795, filed Oct. 12, 1989, now abandoned.

BACKGROUND OF THE INVENTION

The present invention relates to new radiation synovectomy compositions and to the use of such compositions. Certain of the compositions and their methods of preparation are also new.

Over two million people in the United States suffer from rheumatoid arthritis. The major cause of pain and physical disability for these individuals comes from destruction of the diarthroidal or synovial joints. The disease will involve the hands (metacarpophalangeal joints), elbows, wrists, ankles and shoulders for most of these patients, and over half will have affected knee joints. Untreated, the joint linings become increasingly inflamed resulting in pain, loss of motion and destruction of articular cartilage. One medical therapy applied to this disease involves the use of chemicals to attack and destroy the inflamed synovium (chemical synovectomy); however, the agents employed are highly systemically and locally toxic and capable of damaging articular cartilage. Similar toxicity concerns arise when repeated injections of corticoid steroids are used. In several cases where chemical therapy has failed, surgery is employed to remove the inflamed joint lining (surgical synovectomy). However, the difficulty of removing all the diseased synovium often leads to regrowth with recurrence of symptoms. If surgery is successful, freedom from symptoms usually lasts two to five years. When the symptoms reappear, surgical reintervention is not an option due to the presence of fibrosis and scar tissue which result from the previous surgery.

Radiation synovectomy has been used in Europe for many years to substantially ablate or destroy the inflamed synovium. The procedure is simple, involving only the injection of a radionuclide of the appropriate characteristics into the synovial cavity. The primary disadvantage of this technique has been the unacceptable radiation doses to non-target organ systems due to leakage of radioactive material from the cavity and difficulty in delivering a β-particle of the appropriate energy for the size joint being treated. The chemical nature of current radiation synovectomy agents is such that leaked materials tend to be retained by liver, spleen and lymph nodes. The leakage problem is often due either to the difficulty of formulating the correct particle size or to lack of a tight binding of the nuclide to the particle. Another disadvantage is the use of radionuclides that don't have the appropriate beta energy to treat the inflamed synovium.

A radiation synovectomy agent that would not have the foregoing disadvantages would have the following characteristics:

1. The radionuclide used in the agent should have a beta energy sufficient to penetrate and ablate the enlarged synovial tissues, but not so great as to damage underlying articular cartilage or overlying skin. Any accompanying radiation should not generate an unacceptable extraneous radiation dose to the patent. The nuclide used may vary depending on the size of the joint and the beta energy necessary to ablate the synovial tissues in that joint.

2. The radionuclide should be attached to a particle of sufficient size so that it will not leak to any great extent from the diseased joint but still be able to be phagocytized in the synovium of the joint.

3. The binding between the radionuclide and the particle should be essentially irreversible through the course of radiotherapy (usually this duration of therapy is determined by the half life of the particular isotope).

4. The particle should preferably be biodegradable, i.e., it should be removable from the joint by the normal biological degradation mechanisms in the joint, itself, and should be cleared from the body in standard ways in a rapid manner with little or no toxicological effects.

5. If radioactive material should leak from the synovial cavity, the radionuclide should be released in a chemical form that rapidly egresses from the body, as for example, an anion which is excreted efficiently through the renal system. Preferably, the radionuclide would stay attached to a chelate or some portion of the degraded particle if this would facilitate clearance from the body.

An object of the present invention is to provide radiation synovectomy compositions containing a radiation synovectomy agent meeting substantially all of the foregoing criteria.

This invention relates to a radiation synovectomy composition for treating, e.g., by ablation, the inflamed synovium of a synovial joint of a person suffering from rheumatoid arthritis. It comprises a radionuclide or radionuclide complex bound to a substantially insoluble particle as the radiation synovectomy agent in a sufficient amount to provide satisfactory synovectomy when administered with a pharmaceutically acceptable radiation synovectomy vehicle. The radionuclide is a beta emitter that would substantially ablate or destroy the diseased synovium, but will not significantly damage underlying articular cartilages or overlying skin. The radionuclide complex is substantially kinetically stable, but should degradation lead to leakage from the joint after administration, the radioactive material will rapidly clear from the body. A substantially kinetically stable complex as known to those skilled in the art is a complex which under normal biological conditions is kinetically stable, but not necessarily 100 percent kinetically stable in each and every patient application since biological systems vary somewhat. However, the necessary stability of the complex is determinant upon the half-life of the radioisotope being used. After the isotope has decayed to the point of being insignificant, the stability of the complex is no longer important. The particle size of the agent is of sufficient size such that there is essentially little or no leakage of the intact radionuclide complex-particle unit from the synovial joint after administration. Additionally, the size and properties of the particle can be defined and controlled before it is bound to the radionuclide complex resulting in an agent having good synovectomy properties. Also, the binding of the radionuclide complex can be controlled resulting in better reproductivity and more complete binding and better in vivo clearance.

A further feature of the present invention is the use of the radiation synovectomy compositions to treat inflamed synovia of people afflicted with rheumatoid arthritis. Another feature of the present invention is directed to novel radiation synovectomy agents. Another feature of the present invention is that by the nature of the labelling process, any in vivo decomposition that generates joint leakage produces radioactive materials in a form that clear rapidly from the body.

As mentioned, the radiation agent comprises a substantially insoluble particle which is of suitable size as to not substantially leak from the joint after administration. Normally, the size may be from approximately 0.5 to 40 microns. These particles are preferably biodegradable (but can also be degradable by other mechanisms) and not prone to aggregation under the conditions used to prepare or store the radiation synovectomy agent. The particle should have a density of approximately 0.7 to 2.0 gm/ml, preferably from 0.7 to 3.5 gm/ml, and should be suspendable in pharmaceutically acceptable vehicles. Some of the material from which such particles can be made include latex, derivatized polystyrene, silica, alumina, albumin (such as albumin microspheres), other proteins, polycarbonates, cellulose and inorganics, e.g., sulfur (colloid) glass (beads), hydroxyapatites, calcium phosphates or calcium pyrophosphates. For purposes of this application, the term "hydroxyapatite(s)" shall include materials known as hydroxyapatite(s) and also as hydroxylapatite(s). These two terms have been used previously in the literature to refer to the same materials. Examples of hydroxyapatites for this application include matrix prepared from the bones and or teeth of animals and matrix prepared by inorganic synthesis, each being more amorphous than crystalline in composition. This includes calcium-hydroxy-hexaphosphate $(3(Ca_3(PO_4)2)Ca(OH)_2$; also given as $2[Ca_5(PO_4)_3OH])$. The particles have sites on the surface that permit absorption or covalent binding of the radionuclide or radionuclide complex. Such sites can include but are not limited to $—NH_2$, $—SH$, $—OH$, $>C=O$, calcium, hydroxyl, phosphate and similar such sites, and hydrophobic or hydrophilic regions or pockets. In addition to being insoluble, the particles must be non-toxic and preferably non-allergenic. Preferred particles include albumin microspheres, sulfur colloid, hydroxyapatite and hydroxyapatite-like matrix.

Hydroxyapatite like refers to calcium-oxyanion-containing particles including calcium phosphate minerals, apatites and apatite precursors of the general formula $Ca_nM_mX_rY_s$ where M is a metal ion selected from Li, Be, Na, Mg, Al, elements of atomic number 19-32, 37-49, 55-82 or a stoichiometric mixture of metal ions, Y is an oxyanion including tetrahedral oxyanions or their protonated forms, carbonate, or a mixture, thereof and X is a simple anion or carbonate or a mixture of simple anions with or without carbonate, m is 0–10, n is 0–10, y is is $\geq 1$, and r is adjusted as needed to provide charge neutrality.

Examples of suitable anions include $OH^-$; $F^-$; $Br^-$; $I^-$; and $\frac{1}{2}[CO_3^{2-}]$. Examples of other metal ions include chromium (III), manganese (II), iron (II), iron (III), praseodynium (III), neodynium (III), samarium (III), ytterbium (III), gadolinium (III), terbium (III), dysprosium (III), holmium (III), and erbium.

When using hydroxyapatite or hydroxyapatite-like matrix, the particle size thereof becomes important. This is because of reports that hydroxyapatite particles may become phagocytosed and solubilized by synovial fibroblasts. In particular, it is believed that the hydroxyapatite particles are first solubilized by phagocytosis and then dissolved in the acidic environment of secondary lyposomes.

Therefore, it is necessary to establish means to maintain the hydroxyapatite of the radiation synovectomy agent for an effective period of time in the synovial cavity. In particular, the rate of solubilization of the hydroxyapatite should optimally be much slower than the half-life of the radioisotope used in the radiation synovectomy agent. In this manner, the radioisotope may completely decay before dissolution of the hydroxyapatite particle. It has been determined that the rate of solubilization and dissolution of hydroxyapatite is a function of particle size, wherein smaller particles are more quickly phagocytosed and dissolved than larger particles. A complete study of rate of solubilization and dissolution as a function of particle size for hydroxyapatite particles has not yet been carried out. However, studies have suprisingly shown that there is no significant lower limit on particle size. In particular, there have been no problems associated with leakage regardless of particle size. For practicle purposes, a particle size of 0.5 microns or greater is preferred, however, smaller particle sizes would be acceptable. It is believed that this is because of the relatively high charge of hydroxyapatite and the tendency of hydroxyapatite particles to aggregate.

Maximum particle size is approximately 40 microns. If particles are too large, e.g. greater than 40 microns, the particles can not be surrounded by cells and will not be easily phagocytosed and dissolved. This can disadvantagously cause dead fibrous areas too occur in the synovium.

In light of the above, when using hydroxyapatite particles as the particles of the radiation synovectomy agent according to the present invention, it is desirable that the hydroxyapatite particles have a particle size of 0.5 to 40 microns.

The radioisotopes that can be used are those that emit beta particles and are such that after administration will ablate the diseased synovium but will not significantly damage the underlying articular cartilage or overlying skin. These isotopes should have an average beta energy between 0.25–2.75 Mev, with or without an imageable gamma ray, with mean soft tissue penetration of about 0.70 and 25.0 mm, and with a half-life of between 0.05 and 700 hours. Examples of preferred beta emitting isotopes include 198-Au, 188-Re, 186-Re, 177-Lu, 176m-Lu, 175-Yb, 169-Er, 166-Ho, 165-Dy, 156-Sm, 153-Sm, 115m-In, 105-Rh, 90-Y, 51-Cr, 77-As, 67-Cu and 32-P, in addition to others of the lanthanide group such as, 141-Ce, 144-Pr, 147-Nd, 148-Pm, 152-Eu, 153-Gd, 157-Tb and 170-Tm. Preferably the isotope would either have an imageable gamma ray or could be doped with an isotope that would contain an imageable gamma ray. This doping isotope could be of the same or different element providing that its chemistry is sufficiently similar to the beta emitting isotope so that its biodistribution in the present use would be close or identical to the beta emitter. Preferred isotopes include: 186-Re, 188-Re, 90-Y, 153-Sm, 77-As, 105-Rh, 177-Lu, 176m-Lu and 166-Ho.

The radionuclide complexes that can be used are those that are stable before and after administration to the synovium joint. Additionally, if such complex leaks from the joint it will be rapidly cleared from the body. This will be the case even if the complex becomes separated from the insoluble particle. The complexes are formed by complexing the radionuclide under complexing conditions with a suitable ligand to provide a complex with the foregoing properties. Ligands that can be used are preferably polydentate, i.e., containing more than two coordinating atoms per ligand molecule. A coordinating atom is defined as one that has a free pair of electrons which can be bonded to the radionuclide. This atom is preferably separated by two or more atoms from any other coordinating atom. The coordinating atoms are chosen from nitrogen, oxygen, sulfur, phosphorus or carbon with nitrogen and/or oxygen and/or sulfur being the preferred coordinating atoms. Examples of chelates include all phosphonate carboxylate and amine carboxylate ligands, $MAG_3$ (mercaptoacetylglycylglycylglycine), all polycarboxylic acid-amine ligands especially DTPA (diethylenetriaminepentaacetic acid), e.g., EDTA (ethylenediaminetetraacetic acid), DADS (N,N'-bis(mercaptoacetamido)ethylenediamine and $CO_2$-DADS N,N'-bis(mercaptoacetamido)-2,3-diaminopropanoic acid) and their derivatives (see European Application 0173424 and U.S. Pat. No. 4,673,562), mono- and poly-phosphonates, BATs (N,N'-bis(2-mercaptoethyl)ethylene-diamine) and derivatives (see European Applications 0163119 and 0200211), thiosemicarbazones, PnAO and other amine-oxime ligands (See European Applications 0123504 and 0194843), marcocyclic and open chain tetra-, penta-, hexa-, hepta- and octacoordinating nitrogen-containing compounds with or without other coordinating atoms or unsaturation. Examples of preferred phosphonate ligands include but are not limited to those specified in U.S. Pat. Nos. 4,234,562; 3,983,227; 4,497,744; 4,233,284; 4,232,000; 4,229,427; and 4,504,463; preferably HEDP (hydroxyethyldiphosphonate), PYP (pyrophosphate), EDIMP (ethylenediaminetetramethylphosphate), and HMDP (hydroxymethylenediphosphonate).

Other ligands include MAGs, DTPA, BAT, DADS and PnAO type ligands which have been modified so that they are bifunctional, i.e., can coordinate the radionuclide and also be coupled to the particle. Preferred complexes include: $MAG_3$, DADS, hydroxyapatite or hydroxyapatite-like matrix complexed with 186-Re, 188-Re, 105-Rh, 153-Sm or 156-Sm.

The radiation agent of this invention can be prepared by attaching or binding to the particle the desired isotope under standard conditions for attachment. This involves coupling a ligand (either with or without a radioactive atom) to the particle with or without the presence of a spacer between the two units. Generally, the coupling can be done by any group(s) attached to the ligand that is (are) not crucial for complexing the radioisotope in a stable manner. This coupling portion of the ligand may consist of any group that can easily and specifically bind covalently to functional groups on the particle or that may simply adsorb very strongly to the surface of the particle. Examples of the covalent coupling would include aminocarboxylate, carboxylate or phosphonate ligands which would combine with $Ca^{2+}$ at or near the surface of the particle, activated esters of carboxylic acids which would combine covalently to amine groups, to sylates and acid halides which would combine with OH groups and maleimides which would combine with thiol groups, with the thiol, amine and OH groups assumed to be at or near the surface of the particle.

The following methods of preparing the desired radiation synovectomy agent may be used:

(a) The pre-formed method: One of the previously described radionuclide complexes is covalently bonded to one of the previously described particles having functional groups. Step one—a particle of the optimal size, (e.g., 1–10 microns, 5–50 microns) and composition (e.g., hydroxyapatite, hydroxyapatite-like matrix, albumin, polycarbonate, cellulose, glass, latex) and having appropriate residues (amines, hydroxyls, hydroxide, phosphate, carboxylates, thiols) is selected. Step two—a radioisotope (of the appropriate nuclear characteristics) which has been incorporated into a ligand (i.e., a radionuclide complex) is covalently bonded to the particle.

(b) The post-formed method: A ligand is covalently bonded to one of the previously described particles. Thereafter, one of the previously described radioisotopes is incorporated into the covalently bonded complexing ligand, after the radionuclide has been treated in such a way, e.g., using a transfer ligand such as citrate or tartarate to facilitate transfer of the radionuclide to the ligand, to make it bind more readily to the ligand.

Specific examples of methods (a) and (b) above are:

(a) The pre-formed method: A stabilizer (gentisic acid), a reductant (stannous) and a transfer agent (citrate) and the appropriate ligand are placed in a vial under an inert atmosphere. 188-Re or 186-Re as perrhenate is injected into the vial. This solution is heated for 15 to 30 minutes in a boiling water bath. The contents of the vial are removed with a syringe and injected into a second vial which contains the desired particle in an appropriate buffer solution. The contents of the second vial are treated in some fashion (heating, pH change) so as to effect covalent bonding of the metal chelate complex to the particle. Quality controls (tlc) are performed on the contents of this second vial. The labelled particles are suspended in a solution that is physically acceptable for injection.

(b) The post-formed method: Properly sized particles are slurried in a buffer solution with an excess of ligand that is activated in a fashion such that conjugation of the ligand to the particle is effected. This solution containing the resulting particle-ligand moiety is injected into a vial which contains a stabilizer, a transfer ligand and a reductant and into which perrhenate has been added in a previous step. The contents of this second vial are treated in some fashion (e.g., heating) so as to effect covalent attachment of the radiorhenium to the particle-bonded chelate. The labelled particles are suspended in a solution that is physically acceptable for injection.

Preferred agents include:
  186-Re-$MAG_3$-albumin microspheres
  188-Re-$MAG_3$-albumin microspheres
  186-Re-$MAG_3$-sulfur colloid
  188-Re-$MAG_3$-sulfur colloid
  186-Re-DADS-albumin microspheres
  188-Re-DADS-albumin microspheres
  186-Re-DADS-sulfur colloid
  188-Re-DADS-sulfur colloid (c) The pre-formed method: A radiorhenium-HEDP complex is prepared by adding an aliquot of radiorhenium to a solution that contains $\geq 10$ mg HEDP, $\leq 3$ mg of $SnCl_2$, and $\geq 10$ mg of gentisic acid. This solution is heated in either an autoclave at 120° C., or a boiling water bath (or heating block) at 100° C. for 15 min. to 1 hour, or in a microwave oven for 2 minutes. An aliquot of this solution is added to a slurry that contains from 10 to 100 mg of hydroxyapatite particles which have been suspended in water to which a 1% dispersant such as Triton-X, Tween-80 has been added. The slurry is stirred at room temperature for up to 30 min. before the particles are collected and washed by centrifugation and/or filtration. The particles are resuspended in an injectable matrix prior to use as a synovectomy agent.

(d) The pre-formed method: An aliquot of samarium-153 is added to a solution that contains a multidentate ligand, for example, a phosphonate, aminocarboxylate or carboxylate ligand. (See A, B and C below.) The pH of the solution is then raised to approximately 4 or 5. A measured amount of hydroxyapatite is added to this solution and the slurry is stirred at room temperature for up to 30 min. before the particles are collected and washed by centrifugation and/or filtration. The particles are resuspended in an injectable matrix prior to use as a synovectomy agent.

A. Preparation of Citrate Solution
  100 mg Citric acid
  4 ml $H_2O$

Combine and stir.

B. Preparation of $^{153}$Sm-Citrate Transfer Ligand Complex

200 μl $^{153}$ SmCl$_3$

600 μl Citrate solution (25 mg/ml, prepared above)

Vortex and incubate for 30 minutes at room temperature. Adjust pH to 4 or 5.

C. Preparation of $^{153}$Sm Labelled Hydroxyapatite (HA)

To two 15 ml polystyrene centrifuge tubes containing stir bars add in order:

40 mg HA 10–20μ

750 μl H$_2$O

250 μl $^{153}$Sm-citrate transfer ligand complex (prepared above)

Incubate and stir for 15 minutes. Centrifuge, decant and wash particles with saline.

(e) The post-formed method: A specific example of this preparation involves the following process: Hydroxyapatite particles are slurried with a solution that contains an excess of ligand, either phosphonate, carboxylate or aminocarboxylate, (see for example A, B and C above) for up to 30 minutes. The particles are removed by centrifugation or filtration and washed to remove the excess ligand. The ligand bonded particles are then added to a solution containing the radioisotope. If necessary, depending upon the chemical nature of the metal radioisotope, a reductant and/or a transfer agent can be added to this solution. After the formation of the ligand bonded particle-radioisotope composition the particles can be collected and washed by centrifugation and/or filtration. The particles are resuspended in an injectable matrix prior to use as a synovectomy agent.

The radiation synovectomy agents of this invention may be used in any pharmaceutically acceptable radiation synovectomy vehicle. These include those suitable for injection, such as aqueous buffer solutions, e.g., (trishydroxymethyl)aminomethane and its salts, phosphate, citrate, bicarbonate, e.g., sterile water for injection, physiological saline and balanced ionic solutions containing chloride and/or bicarbonate salts of normal blood plasma cations such as calcium, sodium, potassium, magnesium. Other buffer solutions are described in Remington's Practice of Pharmacy, 11th Edition, for example on page 170. Additionally, the vehicle may contain stabilizers, antioxidants and other adjuncts. Stabilizers include gelatin or other materials in stabilizing amounts to prevent aggregation of the particles, antioxidants in antioxidant amounts such as reducing sugars (e.g., fructose, or free acid or metal salts of gentisic acid) ascorbic acid and other adjuvants such as reducing agents, preferably stannous salts, intermediate exchange ligands in exchange amounts such as metal salts of tartrate, gluconate or citrate as well as bulking agents in bulking amounts such as lactose.

The composition may be formulated in a one-step procedure as a lyophilized kit where the radioisotope solution is injected for reconstitution or as an autoclaved or radiation sterilized solution which is then treated with the radioisotope. In this case, the ligand has already been attached to the particle before lyophilization or autoclaving. The product may be formulated in a two-step scheme where the radioisotope is bound to the ligand and then this complex with or without purification as necessary is combined with the particles to give the final radiation synovectomy composition. Any of these steps may require heating and any of the intermediates or final products may require purification before use.

The concentration of the radiation synovectomy agent in the pharmaceutically acceptable vehicle varies with the particular use. A sufficient amount is present to provide satisfactory radiation synovectomy. This amount will vary with the physical properties of the isotope being used. For example, when using 186-Re for radiation synovectomy of the hip, a sufficient concentration is 2 to 5 mCi and preferably from 3 to 4 mCi. When it is used for the radiation synovectomy of the wrist joints, it is used in an amount from 1 to 3 mCi and preferably from 1 to 2 mCi. When using 153-Sm for radiation synovectomy, the concentration used is roughly the same as that described for 186-Re within a factor of two.

The radiation synovectomy composition is administered so that preferably it remains substantially in the joint for 20 half-lifes of the isotope although shorter residence times are acceptable as long as the leakage of the radionuclide is small and the leaked radionuclide is rapidly cleared from the body.

The radiation synovectomy compositions may be used in the usual way for such procedures. For example, in the case of the treatment of a knee-joint, a sufficient amount of the radiation synovectomy composition to provide adequate radiation synovectomy is injected into the knee-joint. There are a number of different techniques which can be used and the appropriate technique varies on the joint being treated. An example for the knee joint has been excerpted below from *Nuclear Medicine Therapy*, J. C. Harbert, J. S. Robertson and K. D. Reid, 1987, Thieme Medical Publishers, pages 172–3.

Strict asepsis is essential. The area to be aspirated and/or injected should be cleansed and prepped as for a spinal tap.

The injection site is selected by first obtaining radiographs in two planes with the joint position at the injection angle. These are used to correlate easily palpable bony landmarks as a guide for needle placement. Major nerves, vessels and tendons should be avoided. Extensor surfaces are the preferred injection sites. The specific area of the joint to be injected is then marked with firm pressure by a ballpoint pen which has the writing tip retracted. This will leave an impression lasting 10 to 30 minutes. The area is carefully cleansed with Betadine solution and the injection site is anesthetized with 1% xylocaine. The injection needle is then inserted through the ballpoint impression, using care to avoid hitting the cartilage. Following insertion, the needle position is checked fluoroscopically using a few milliliters of contrast material. Alternatively 1 mCi (37 MBq) of $^{99m}$Tc-sulfur colloid can be injected prior to injecting the therapeutic dose. The joint is then scanned to assure distribution throughout the joint space. This is an important precaution, because loculated distribution is probably a common cause of treatment failure. Following injection of radiocolloid the needle is flushed with 10 to 20 mg triamcinolone and the needle withdrawn. The joint is then splinted or the patient confined to bed rest for 48 hours to minimize leakage from the joint space (in the case of 165Dy-macroaggregates, 7 hours bed rest is deemed sufficient.)

The knee is the easiest joint to inject. The patient should be in a supine position with the knee fully extended. The puncture is made 1 to 2 cm medial to the medial margin of the patella using an 18-gauge by 1.5 in. needle directed slightly inferiorly and toward the joint space. The joint space should be entered and easily aspirated. If osteophytes make this approach difficult, the knee may be injected with the patient sitting and the knee fixed. In this case, the needle is placed beneath the distal border of the patella and directed straight posteriorly or slightly superiorly toward the joint cavity.

In most cases after the joint has been injected, it is either (1) moved to allow homogeneous distribution of the radiation synovectomy agent and then immobilized and shielded with appropriate radioactive shielding for a period of time related to the half-life of the isotope or (2) simply immobilized and shielded without working the joint.

It is to be understood that the invention is not to be limited to the exact details of operation or exact compounds, compositions or procedures shown and described, as obvious modifications and equivalents will be apparent to one skilled in the art, and the invention is therefore to be limited only by the scope of the appended claims.

What is claimed is:

1. A radiation synovectomy composition for treating inflamed synovium in a joint containing a radionuclide complex bound to a hydroxyapatite-like matrix as the radiolabelled synovectomy agent in a sufficient amount to provide satisfactory synovectomy of the inflamed synovium together with a pharmaceutically acceptable vehicle, said radionuclide being a beta emitter that will substantially ablate the inflamed synovium, but not significantly damage underlying articular cartilage, said radionuclide complex being substantially kinetically stable, and if said radionuclide or radionuclide complex leaks from said joint it will be excreted from the body, said agent having a particle size such that there is substantially no leakage of the radionuclide complex from the joint after administration.

2. A composition according to claim 1, wherein said complex is selected from the group consisting of a 188-Re complex, a 186-Re complex, a 153-Sm complex and a 156-Sm complex.

3. A composition according to claim 2, wherein said complex is selected from the group consisting of 188-Re MAG$_3$ complex, 186-Re MAG$_3$ complex, 188-Re DADS complex, 186-Re DADS complex, 188-Re HEDP complex, 186-Re HEDP complex, 153-Sm HEDP complex and 156-Sm HEDP complex.

4. A composition according to claim 1, wherein said complex is 186-Re HEDP, 188-Re HEDP, 153-Sm HEDP or 156-Sm HEDP bound covalently to the hydroxyapatite-like matrix through the pendant calcium group.

5. A composition according to claim 4, wherein said hydroxyapatite-like matrix has a particle size of about 0.5 to 40 microns.

6. A method for radiation synovectomy of the inflamed synovium in a joint wherein a radiation synovectomy composition containing a radiation synovectomy agent in a pharmaceutically acceptable radiation synovectomy vehicle is administered to the inflamed synovium in a sufficient amount to provide radiation synovectomy, the improvement comprising utilizing as the radiation synovectomy composition a composition containing a radionuclide complex bound to a hydroxyapatite-like matrix as the radiolabelled synovectomy agent in a sufficient amount to provide satisfactory synovectomy of the inflamed synovium together with a pharmaceutically acceptable vehicle, said radionuclide being a beta emitter that will substantially ablate the inflamed synovium, but not significantly damage underlying articular cartilage, said radionuclide complex being substantially kinetically stable, and if said radionuclide or radionuclide complex leaks from said joint, it will be excreted from the body said agent having a particle size such that there is substantially no leakage of the radionuclide complex from the joint after administration.

7. A method according to claim 6, wherein said complex is selected from the group consisting of a 188-Re complex, a 186-Re complex, a 153-Sm complex, and a 156-Sm complex.

8. A method according to claim 7, wherein said complex is selected from the group consisting of 188-Re MAG$_3$ complex, 186-Re MAG$_3$ complex, 188-Re DADS complex, 186-Re DADS complex, 188-Re HEDP complex, 186-Re HEDP complex, 153-Sm HEDP complex and 156-Sm HEDP complex.

9. A method according to claim 8, wherein said complex is 188-Re HEDP, 186-Re HEDP, 153-Sm HEDP or 156-Sm HEDP bound covalently to the hydroxyapatite-like matrix through the pendant calcium group.

10. A method according to claim 8, wherein said complex is 188-Re HEDP, 186-Re HEDP, 153-Sm HEDP or 156-Sm HEDP bound to the hydroxyapatite-like matrix.

11. A method according to claim 6, wherein said hydroxyapatite-like matrix has a particle size of about 0.5 to about 40 microns.

12. A therapeutic radiation synovectomy method comprising: injecting into the synovium of a patient a therapeutically effective amount of a pharmaceutical composition comprising a chelate sorbed to a calcific matrix, wherein the chelate is a beta-emitting radionuclide complexed with a chelating ligand, wherein the calcific matrix is particulate and having a particle size such that there is substantially no leakage of the radionuclide complex from the synovium.

* * * * *